United States Patent [19]
Marek

[11] Patent Number: 5,086,643
[45] Date of Patent: Feb. 11, 1992

[54] SYSTEM AND METHOD FOR DETERMINING MULTI-PHASE RELATIVE PERMEABILITY OF A SUBTERRANEAN RESERVOIR

[75] Inventor: Benjamin F. Marek, Coppell, Tex.
[73] Assignee: Mobil Oil Corporation, Fairfax, Va.
[21] Appl. No.: 584,222
[22] Filed: Sep. 18, 1990
[51] Int. Cl.$^5$ ............................................. G01N 15/08
[52] U.S. Cl. ............................................................. 73/38
[58] Field of Search ............................................... 73/38

[56] References Cited

U.S. PATENT DOCUMENTS

| | | | |
|---|---|---|---|
| 2,345,935 | 4/1944 | Hassler | 73/38 |
| 3,839,899 | 10/1974 | McMillen | 73/38 |
| 4,157,472 | 6/1979 | Beck et al. | 250/445 |
| 4,283,629 | 8/1981 | Habermehl et al. | 250/445 |
| 4,399,509 | 8/1983 | Hounsfield | 364/414 |
| 4,422,177 | 12/1983 | Mastronardi et al. | 378/17 |
| 4,531,404 | 7/1985 | Phelps et al. | 73/38 |
| 4,649,483 | 3/1987 | Dixon, Jr. | 364/422 |
| 4,672,840 | 6/1987 | Cullick | 73/38 |
| 4,688,238 | 8/1987 | Sprunt et al. | 378/4 |
| 4,722,095 | 1/1988 | Muegge et al. | 378/4 |
| 4,782,501 | 11/1988 | Dixon, Jr. | 378/4 |
| 4,868,751 | 9/1989 | Dogru | 364/422 |
| 4,907,448 | 3/1990 | Givens | 73/153 |

*Primary Examiner*—Hezron E. Williams
*Assistant Examiner*—Joseph W. Roskos
*Attorney, Agent, or Firm*—Alexander J. McKillop; Charles J. Speciale; Michael J. Mlotkowski

[57] ABSTRACT

A system and method for determining multi-phase relative permeability characteristics of a porous media sample obtained from a subterranean reservoir. The porous media is placed in a confining flow cell assembly and the pressure drop across the porous media is measured during multi-phase fluid flooding. A computed tomography (CT) scanning system provides images of the density distribution within the core sample. Fluid saturation is determined from these CT images as well as from material balance and pressure drop data to determine the relative permeability of the subterranean reservoir.

20 Claims, 6 Drawing Sheets

SYSTEM AND METHOD FOR DETERMINING MULTI-PHASE RELATIVE PERMEABILITY OF A SUBTERRANEAN RESERVOIR

FIELD OF THE INVENTION

The present invention relates to a system and method for determining certain characteristics of porous material taken from subterranean formations and, more particularly, to a system and method for determining multi-phase relative permeability of a core sample taken from a subterranean hydrocarbon-bearing reservoir.

BACKGROUND OF THE INVENTION

In the production of minerals, such as oil and gas, certain properties of a subterranean reservoir must be determined. One of the most important of these properties is the permeability of the reservoir. Permeability is a measure of the ability of fluids to pass through porous media. The original work on permeability was carried out by H. Darcy, who studied the flow rates of springs at Dijon, France. Muskat and Boset advanced the work of Darcy, their efforts culminating in the formulation of Darcy's law:

$$Q = \frac{K(P_1 - P_2)A}{\mu L}$$

where:
- $Q$ = rate of flow
- $K$ = permeability
- $(P_1-P_2)$ = pressure drop across sample
- $A$ = cross-sectional area of sample
- $L$ = length of sample
- $\mu$ = viscosity of fluid.

When a single fluid phase completely saturates the pore space of a porous media, permeability is referred to as absolute permeability. The effective permeability refers to saturations of less than 100 percent. The terms $K_o$, $K_w$ and $K_g$ are used to designate the effective permeability with respect to oil, water and gas, respectively. Relative permeability is the ratio of effective permeability for a particular fluid at a given saturation to a base permeability.

As demonstrated by Darcy's law, the permeability of a material is inversely proportional to the flow resistance offered by the material. Normally, permeability is determined by taking core samples from the reservoir and carrying out well-defined measurement techniques on the samples. There are several techniques available for making such measurements, many of which are described in *PETROLEUM PRODUCTION ENGINEERING-DEVELOPMENT* by L. C. Uren, Fourth Edition, McGraw-Hill Book Company, Inc., 1956, pps. 660–669. Another standard reference is American Petroleum Institute, *API RECOMMENDED PRACTICE FOR CORE-ANALYSIS PROCEDURE*, API RP40, 1960.

In addition to these well known techniques, a more recently applied technique involves the use of computed tomography (CT) technology. Although only recently applied in the area of energy research, CT technology has been used in the medical field for several years. CT scanning instruments produce a cross-sectional view through the subject material along any chosen axis. The advantages of CT scanning over conventional radiography is found in its ability to display the electron density variations within the object scanned in a two-dimensional X-ray image. In medical CT scanners, an X-ray source and a detector array circle a patient in a period of about 2 to 9 seconds to produce an image having a maximum resolution of 0.25 mm in the X-Y plane. This plane can be moved in discrete intervals to obtain information in three dimensions. For more details of such medical CT scanners, reference may be made to U.S. Pat. No. 4,157,472 issued to Beck, Jr. and Barrett and U.S. Pat. No. 4,399,509 issued to Hounsfield.

Several other applications of CT scanning can also be made. For example, in an article entitled, "Computed Tomographic Analysis of Meteorite Inclusions", Science, pps. 383–384, Jan. 28, 1983, there is described the non-destructive testing of meteorites for isotopic anomalies in calcium- and aluminum-rich inclusions of heterogeneous materials, such as Allende. The CT scanning equipment described in the article is the Deltascan 2020 from Technicare. In a further application, CT scanning has been applied to the non-destructive testing of wood materials, such as for disease living in trees, see U.S. Pat. No. 4,283,629 issued to Habermehl. In a yet further application, CT scanning has been applied to the examination of non-living objects, such as motors, ingots, pipes, etc., see U.S. Pat. No. 4,422,177 issued to Mastronardi, et al.

More recently, CT scanning technology has been applied to the field of energy research for examining the interior of stationary or slowly changing earth materials, such as coal, shale and drilling cores. Processes involved in coal gasification and combustion have been monitored using time-lapse CT imagery to observe changes in density (e.g. thermal expansion, fracturing, emission of gases, consumption by combustion and the like) during progressive heating in a controlled atmosphere. Core flooding experiments can now be carried out with CT scanning to aid in enhanced oil recovery and fluid mobility control. For example, the permeability of materials within core samples to various fluids at varying conditions of temperature and pressure can be determined. Such experiments involve flushing a fluid through a core sample and monitoring the shape of the fluid fronts. By subtracting the images of the cores before and after flooding, the exact shape of the fluid front is determined. Such core flooding experiments allow the interior of the core sample to be observed without disturbing the sample. The sweep efficiency and flow paths of fluids of interest may now be studied on the scale of millimeters. The penetration of X-rays allows experiments to be performed with up to four-inch diameter cores samples.

Drilling fluids can be analyzed by CT scanning as such fluids are characterized by high-density brines, various organics and several compositionally different weighting agents. Formation damage can be investigated since CT scanning can detect migration of clays, absorption of organics and the reversibility of completion fluid penetration. Shale oil recovery can also be aided as CT scanning could detect penetration by solvents and could directly measure structure changes on retorting.

U.S. Pat. No. 4,649,483, issued to Dixon, discloses a method for determining fluid saturation in a porous media through the use of CT scanning. Multi-phase fluid saturation in a sample of porous media is determined through computer tomographic scanning. The sample is scanned with X-rays of differing energies in both the fluid saturated and the fluid extracted states. Each of the extracted fluids is also scanned at differing X-ray energies. The computed tomographic images produced are utilized in the determination of the X-ray mass attenuation coefficients for the sample and the extracted fluids. From these mass attenuation coefficients, the weight fractions and volume fractions of each of the extracted fluids are determined. U.S. Pat. No. 4,649,483 is incorporated by reference in its entirety for all that it discloses.

U.S. Pat. No. 4,688,238, issued to Sprunt et al. discloses a method for using CT scanning over a range of confining pressures on a core sample to determine pore volume change, pore compressibility and core fracturing. A core sample with a surrounding elastic jacket is placed in a confining pressure cell. Pressure is applied to the cell to press the jacket into contact with the surface of the sample. The pressure in the cell is increased stepwise over a plurality of pressure points. The sample is scanned at a plurality of locations with X-rays at each of the pressure points. Computed tomographic images of the sample are produced for each of the X-ray scans. The conformance of the jacket to the sample is determined from these computed tomographic images. From such conformance, a range of confining pressures is determined over which pore volume and pore compressibility of the sample are measured without being affected by improper conformance of the jacket to the surface of the sample. Also rock fracturing is determined form the pressure at which crushing of the sample destroys permeable channels within the sample and results in a permeability measurement that is lower than the actual permeability measurement.

Relative permeability plays a very important role in describing the fluid flow in oil and gas reservoirs. Two methods of measurement are practiced by industry; namely, steady-state and dynamic displacement. In each method a cylindrical core is saturated with water or brine, then oil flooded to irreducible water saturation. Subsequently, the core is waterflooded or brine flooded and the pressure drop across the core is measured along with the oil and water or brine production. The average saturations within the core are determined from the overall material balance. The steady-state method requires lengthy measurement times because it requires stabilization of the fluid flow. The dynamic displacement method overcomes this, however, it suffers from capillary end effects. Hence the displacement method is generally only effective for high flow rates.

U.S. Pat. No. 4,672,840, issued to Cullick, discloses a method and system for determining fluid volumes of a two-phase effluent flow through a porous material in order to determine permeability characteristics. A two-phase flow condition is established through the porous material, such as a core sample taken from a subterranean hydrocarbon-bearing reservoir. One phase is a liquid hydrocarbon phase, the other an insoluble displacing liquid phase. After exiting the core sample, the two-phase fluid is collected in a container where it separates into an overlying fluid phase, such as an oil phase, and an underlying fluid phase, such as a water phase. A fluid level monitor is positioned in the container. When the air-fluid interface at the top of the overlying fluid phase rises to a first position in the upper portion of the container, drainage of the underlying fluid phase is initiated. The time is measured during which the fluid-fluid interface of the overlying and underlying fluid phases is lowered to a second position near the bottom of the container. The time is also measured during which the air-water interface of the top of the overlying fluid phase is lowered to the same second position near the bottom of the container. The volumes of each of the two fluid phases are determinable from the time measurements and the drainage flow rate of the fluid, such volumes being representative of fluid saturation in the core sample from which core sample permeability is thus determined.

U.S. Pat. No. 4,868,751, issued to Dogru et al., relates to a method for determining relative permeability of a core sample taken from a subterranean hydrocarbon-bearing reservoir. In the method disclosed therein, pressure and fluid saturation are measured at a plurality of corresponding positions along the core before and during fluid flooding of the core. From these measurements the relative permeability of the reservoir is determined. At the start of the relative permeability measurement, the core is fully saturated with a known weight or volume of a saturating fluid, such as an oil or a brine. Dual energy X-ray CT scans are taken at a plurality of scan positions. Thereafter, the core saturation is altered through the core by flowing a displacing fluid, other than that with which the core is saturated, such as an oil, water or brine, and both saturation and pressure measurements made. U.S. Pat. No. 4,868,751 is hereby incorporated by reference for all that it discloses.

Three-phase relative permeability characteristics of reservoir rocks are usually determined from one of several mathematical models based on two-phase relative permeability data. There is a very limited amount of three-phase data available to test the validity of these models. Procedures available to industry for obtaining three-phase data are complex, and in many instances, the assumptions and errors in generating the data are suspect. As such, a need exists to design and develop a test system and method for obtaining reliable three-phase flow saturation data.

It is therefore an object of the present invention to provide a new method and system for determining the relative permeability of a subterranean reservoir which can be used to determine three-phase relative permeability characteristics of core samples obtained from such a reservoir.

SUMMARY OF THE INVENTION

In accordance with the present invention there is provided a system and method for determining multi-phase fluid saturation and relative permeability of porous media obtained from a subterranean reservoir. The system comprises: means for containing the porous media, said media containing means having a fluid inlet positioned at a first end thereof and a fluid outlet positioned at a opposing second end thereof; a fluid separatory vessel for separating the multi-phase fluid by density into at least a first fluid phase and a second fluid phase, said vessel having an inlet in fluid communication with said fluid outlet of said media containing means and at least a first outlet and a second outlet, wherein said first outlet and said second outlet of said vessel are positioned to permit withdrawal of the separated first fluid phase and the separated second fluid phase, respectively; means for measuring pressure within said media containing means; a first pumping means in fluid communication with said first outlet of said fluid separatory vessel for withdrawing the separated first fluid phase therefrom for transfer to said fluid inlet of said media containing means; a second pumping means in fluid communication with said second outlet of said fluid separatory vessel for withdrawing the separated second fluid phase therefrom for transfer to said fluid inlet of said media containing means; means for measuring fluid flow of the separated first fluid phase in transfer from said first outlet of said fluid separatory vessel to said fluid inlet of said media containing means; and means for measuring fluid flow of the separated second fluid phase in transfer from said second outlet of said fluid separatory vessel to said fluid inlet of said media containing means Also provided is a method for determining multi-phase relative permeability of a porous media, comprising the steps of: establishing a multi-phase fluid flow condition through the porous media, the multi-phase fluid having at least a first phase having a first density and a second phase having a second density; measuring the pressure drop across the length of the porous media; collecting the multi-phase fluid in a fluid separatory vessel; separating the multi-phase fluid by density within the fluid separatory vessel; recirculating at least one phase of the multi-phase fluid so separated to the porous media; repeating the aforementioned steps until steady-state flow conditions by phase are obtained; determining fluid saturation within the porous media; and determining the relative permeability of the porous media from said measurements of pressure and fluid saturation.

Therefore, it is an object of the present invention to provide a system and method for determining the multi-phase fluid saturation characteristics of porous media.

It is another object of the present invention to provide a system and method for determining the three-phase fluid saturation characteristics of core samples obtained from an oil-bearing reservoir in which one of the fluid phases is a gaseous fluid phase.

It is a further object of the present invention to provide a system and method for determining the multi-phase relative permeability characteristics of porous media.

It is yet another object of the present invention to provide a system and method for determining the three-phase relative permeability characteristics of core samples obtained from an oil-bearing reservoir in which one of the fluid phases is a gaseous fluid phase.

Other objects and the several advantages of the present invention will become apparent to those skilled in the art upon a reading of the specification and the claims appended thereto.

BRIEF DESCRIPTION OF THE DRAWINGS

The actual construction, operation and advantages of the present invention will be better understood by referring to the following drawings in which like numerals identify like elements and in which.

DETAILED DESCRIPTION OF THE INVENTION

Figure 1:
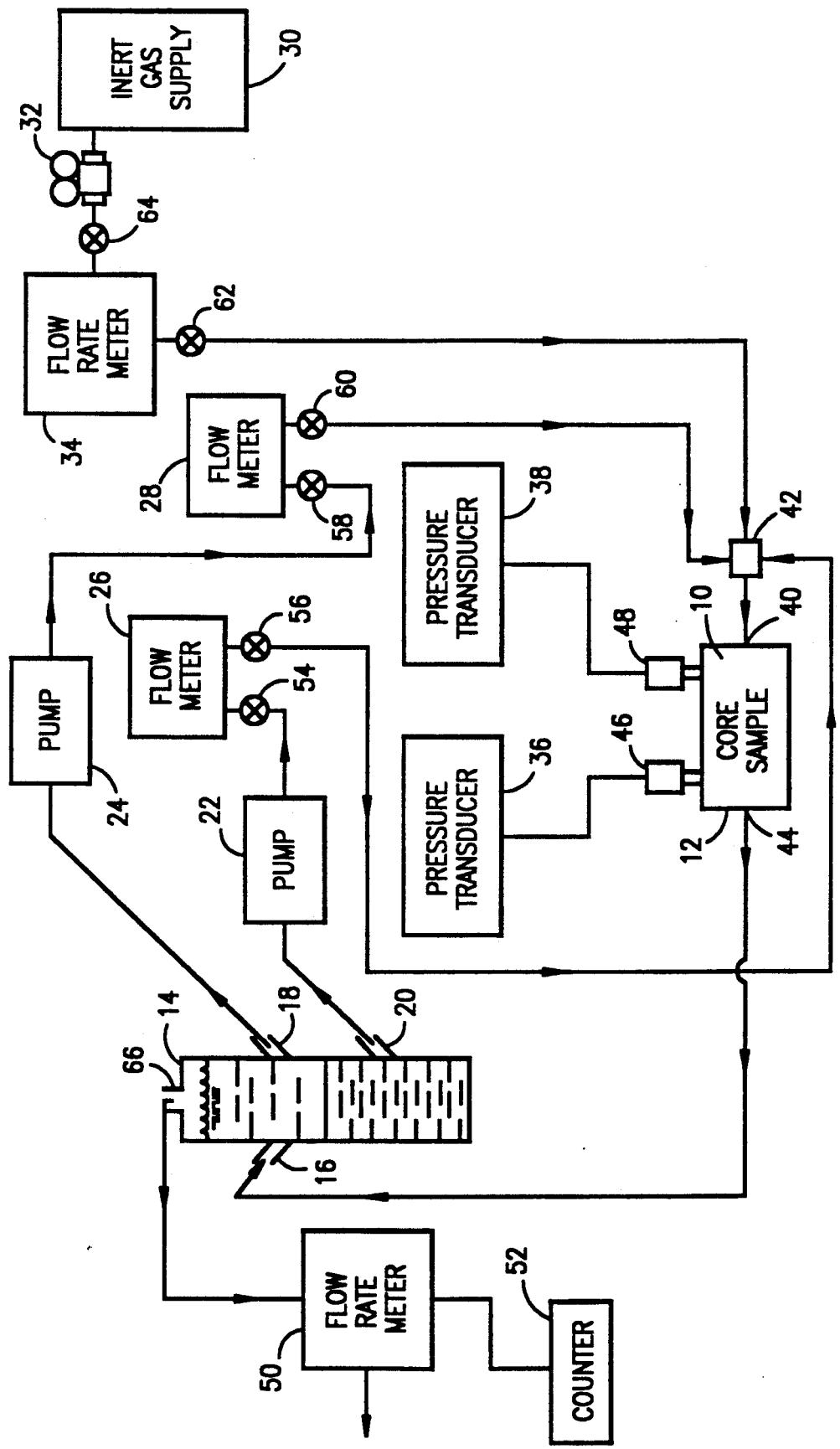
FIG. 1 is a schematic representation of a system for carrying out multi-phase relative permeability characteristic determinations on a porous media core sample in accordance with the present invention.

The present invention is best understood by reference to the appended figures, which are given by way of example and not of limitation. Referring now to FIG. 1, a schematic representation of a system for carrying out multi-phase relative permeability characteristic determinations on porous media is presented. A core sample 10 of a porous material is taken from a subsurface formation and mounted within containing means 12. Containing means 12 may be one of the well-known flow cell assemblies developed for the analysis of core sample properties. One such cell assembly is disclosed in U.S. Pat. No. 2,345,935, issued to Hassler. Another cell assembly is disclosed in U.S. Pat. No. 4,531,404, issued to Phelps and Sampath. Still more preferred is a novel X-ray transparent flow cell assembly depicted in FIGS. 2 and 3 and described in detail hereinbelow.

Core sample 10 is initially saturated with a liquid hydrocarbon, such as oil; an insoluble displacing fluid, such as water or brine; a gaseous fluid, such as nitrogen; or a combination thereof. Thereafter, a multi-phase fluid flow is established through core sample 10 by the continuous injection at fluid inlet 40 of containing means 12 of a combination of at least two fluids, those fluids selected from the group consisting of a liquid hydrocarbon, an insoluble displacing fluid or a gaseous fluid. The multi-phase fluid so injected flows out of core sample 10 and containing means 12 at fluid outlet 44 and is transported through suitable tubing or piping to fluid separatory vessel 14. Fluid separatory vessel 14, as may be seen, has an inlet 16 for receiving the fluid transported thereto and a plurality of outlets 18, 20 and 66. As can be appreciated, fluid separatory vessel 14 functions so as to separate the multi-phase fluid entering inlet 16 by density into at least a first fluid phase and a second fluid phase. When the multi-phase fluid contains two liquid phases, such as an oil phase and a water or brine phase, as well a gaseous phase, the fluid outlets 18, 20 and 66 may be advantageously positioned as shown schematically in FIG. 1 so as to enable the separate withdrawal of each fluid phase. To permit the accurate measurement of fluid, by phase, contained within fluid separatory vessel 14, fluid separatory vessel 14 may be constructed of glass, or other transparent material, with accurate graduated markings positioned thereon. Such a three-phase separation system was developed which is accurate to 0.1 cc liquid volume.

As is preferred in the practice of the present invention and shown in FIG. 1, the system employs a "closed" liquid system which enables a minimum total liquid volume to be used. The use of a closed liquid system allows for a substantial improvement to be achieved in the precision of measuring changes in the oil and water or brine volumes (saturations) in the core sample. Liquid pumps 22 and 24 are preferred to operate in the range of 0.05 to 2.0 cc/min, with an accuracy of 1.0 percent of the actual reading. Preferred are pumps of the reciprocating type, an example of which is the commercially available Constametric II pump. Advantageously, suitably accurate flow meters 24 and 26 are integral to the Constametric II pump.

Still referring to FIG. 1, it may be seen that the gaseous phase supply and control system is not a closed system. Gas, which may be inert for safety reasons and to minimize chemical reactivity, is supplied from tank 30, which may, as is preferred be a compressed gas cylinder containing nitrogen or the like. Gas flow is regulated by regulator 32. Flow rate meter 30 is selected to permit gas injection volumes as low as 1.0 cc/min with an accuracy of 0.1 cc/min. Flow rate meter 30 is a commercially available unit. Two sets of piezoelectric transducers 46 and 48 and transducer modules 36 and 38 are used. As is preferred, each set employed has one transducer covering a pressure range of 0.1 to 15 psi and another covering a range of 1 to 100 psi. The two transducers comprising each set are connected in series which permits monitoring the flow pressures from 0.1 psi to 100 psi with an estimated accuracy of 1.0 percent of the reading. To determine the amount of gaseous fluid contained within the multiphase effluent flow emanating from outlet 44 of containing means 12, another flow rate meter 50 is placed in fluid communication with outlet 66 of fluid separatory vessel 14. Counter 52 is employed to determine the volume of gas passing through flow rate meter 50 during a measurement period.

Figure 2:
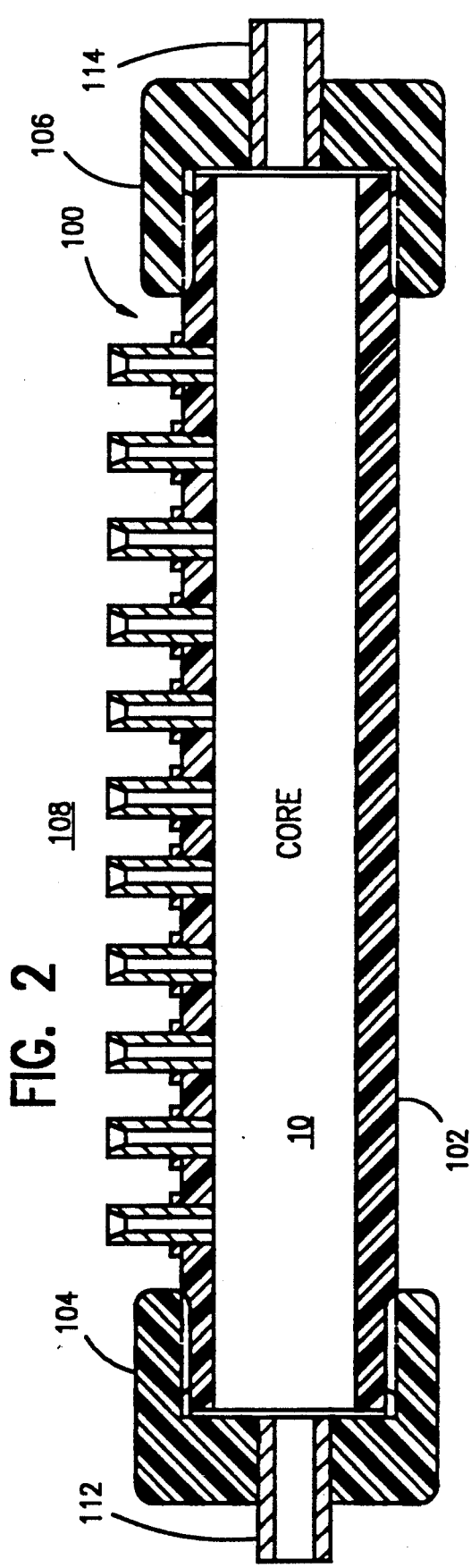
FIG. 2 is a cross-sectional side view of a flow cell assembly for use in carrying out measurements in accordance with the present invention.
Figure 3:
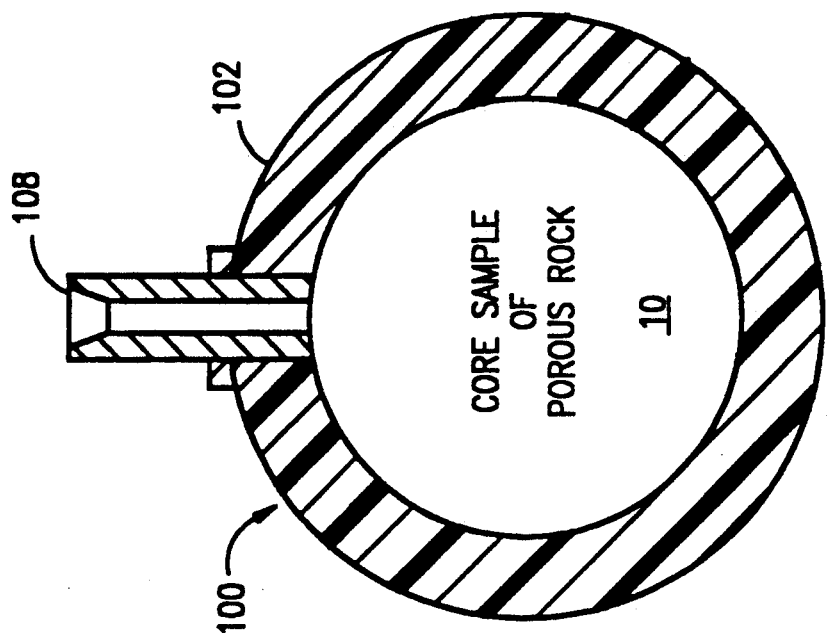
FIG. 3 is a cross-sectional end view of a flow cell assembly, with flow heads removed, for use in carrying out measurements in accordance with the present invention.

It is desirable when conducting the method of the present invention to preserve the rock-fluid and fluid-fluid integrity of the core sample and to scale the flow and pressure parameters to reasonably match those of the reservoir to be modeled. A special core mounting procedure and core containing means was developed to preserve the wettability and physical integrity of the porous media sample. Referring now to FIGS. 2 and 3, the method consists of mounting the fresh core sample in an X-ray transparent polymeric tube 102. Suitable tube materials include those selected from the group of polymeric esters of methacrylic acid, such polymeric esters of methacrylic acid given by the relationship:

CH₂C(CH₃)COOR where: R is methyl, ethyl, n-butyl, isobutyl, or combinations of these alkyl groups.
Particularly preferred is the commercially available material marketed under the trademark of Lucite ® by DuPont Co. of Wilmington, Del. Polymeric tube 102, containing core sample 10, is then subjected to a confining pressure of approximately 1000 psi, at a 230° F. temperature, to form a tight seal around the circumference of porous media core sample 10. An advantage of the method of the present invention is that it does not place excessive localized stress on core sample 10, nor does it affect the wettability of the sample. Moreover, core sample 10 need never be removed from polymeric tube 102, throughout the complete battery of tests required to be performed to assess the characteristics of that porous media sample. Pressure taps 108, flow heads 104 and 106, flow inlet 112, flow outlet 114, and any auxiliary connections are machined from a plastic material, such as the material preferred for use for polymeric tube 102, and assembled to polymeric tube 102 to form flow cell assembly 100. As such, a flow cell such as the aforementioned Hassler cell is not required.

As shown, a plurality of pressure taps 108 may be provided to assess the pressure gradient across the core sample during testing. Such an arrangement advantageously permits flow cell assembly 100 to be employed in the method disclosed in U.S. Pat. No. 4,868,751, discussed above. As can be appreciated by those skilled in the art, additional sets of pressure transducers and transducer modules, not shown in FIG. 1, would be required to assess pressure gradient. A particularly significant benefit as it relates to the present invention stems from the fact that the total assembly is compatible with CAT scanning equipment for X-ray tomography tests.

Figure 4:
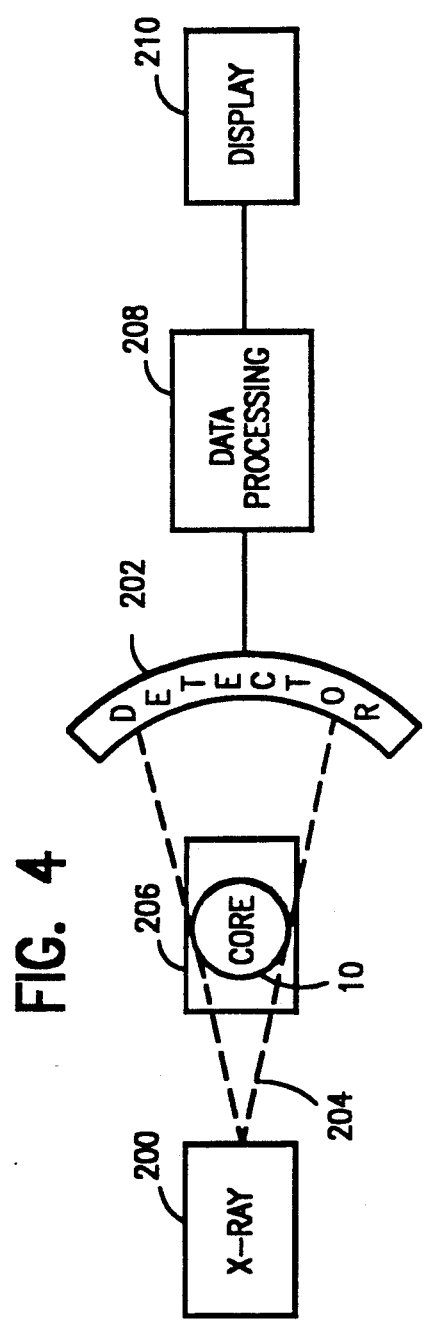
FIG. 4 illustrates a computed tomography system for use in carrying out multi-phase saturation measurements in accordance with the method of the present invention.

As indicated, fluid saturation may be measured using x-ray attenuation. In one embodiment of the present invention, the computed tomography (CT) scanning system of FIG. 4 may be utilized. This CT scanning system produces a display or image of the density distribution in a cross-section or transverse slice of the core. As shown schematically in FIG. 4, X-ray energy provided by the X-ray tube 200 passes through the core sample 10 and falls on the detector array 202. Rotation and indexing of core sample 10 within the X-ray fan beam 204 is provided by the gantry 206. After a desired number of scans are completed for each sample slice, the core is indexed to place the next sample slice within the path of the X-ray fan beam 204. Signals from detector 202 are applied through data processing unit 208 to display 210 where the CT images are viewed. While not forming a part of the present invention, such a CT scanning system is used in accordance with the method of the present invention to determine saturation of the pore spaces within the core sample. The CT scanning system of the aforementioned patent to Dixon, Jr. is particularly applicable to the method of the present invention in that Dixon Jr. describes in detail the steps of determining the multi-phase fluid saturation of a core sample from a subterranean reservoir utilizing X-ray mass attenuation coefficients for the core sample obtained from the plurality of X-ray images. From these X-ray mass attenuation coefficients, the weight fractions and volume fractions of each phase of the fluid is determined.

Figure 5:
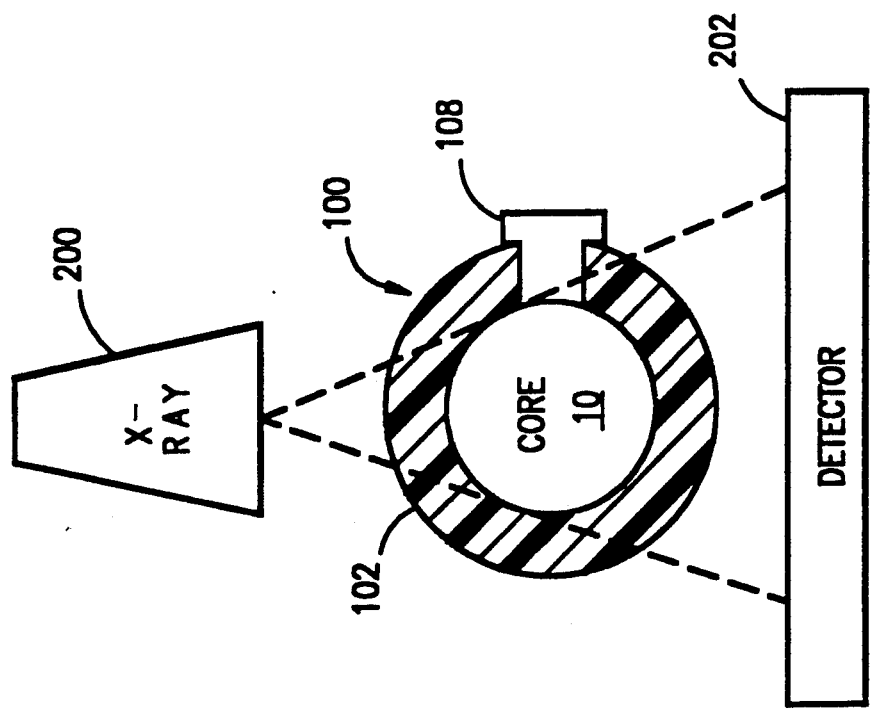
FIG. 5 is a schematic representation showing the orientation of a core sample mounted in the core sample holder assembly of FIG. 2 and subjected to X-ray scanning by the computed tomography system of FIG. 4.

In using the system and method described in Dixon, Jr., the orientation of the CT system with respect to the core pressure holder is shown in FIG. 5. Core sample 10, is mounted within polymeric tube 102 of flow cell assembly 100. In FIG. 5, flow cell assembly 100 is shown in a simplified cross-sectional pictorial view with a single pressure tap 108 leading to the core 10. The CT scans are positioned on either side of the pressure taps, such as pressure tap 108 shown. The X-ray slice that the CT scan makes through the core 10 should be at least one half a CT scan slice width away from the edge of the pressure tap to avoid artifacts. For example, if the slice width is 3 millimeters, the CT scan slice should be 1.5 millimeters from the edge of the pressure tap. Reference X-ray CT scans are obtained at known end point saturations on either side of each of the plurality of pressure taps at two or more X-ray energies for each scan position to allow dual-energy scanning. Such reference end point saturation conditions include oven dry, fully water or brine saturated, fully gas saturated and fully oil saturated. The average intensity of the resulting CT images establish the CT numbers for the core sample fluids. These CT numbers are utilized in accordance with the teaching of the aforementioned U.S. Patent to Dixon, Jr. to determine the saturation for each CT scan slice.

The invention is further illustrated by the following non-limiting examples:

EXAMPLES

Example 1

This example demonstrates the utility of the system and method of the present invention in two-phase fluid testing.

Fluids used in this example tests were selected to represent interfacial tension, gravity, density, and viscosity typical of a hydrocarbon reservoir. Hexadecane and barium bromide were selected as the oil and brine phases, respectively. Berea sandstone was selected as the core sample for the first series of tests. The Berea sample was mounted in polymeric tube 102, using the method described above, to form flow cell assembly 100. The Berea sample, installed in polymeric tube 102, was CAT scanned dry, 100 percent saturated with hexadecane, and 100 percent saturated with barium bromide to obtain calibration data for X-ray tomography analysis.

Figure 6:
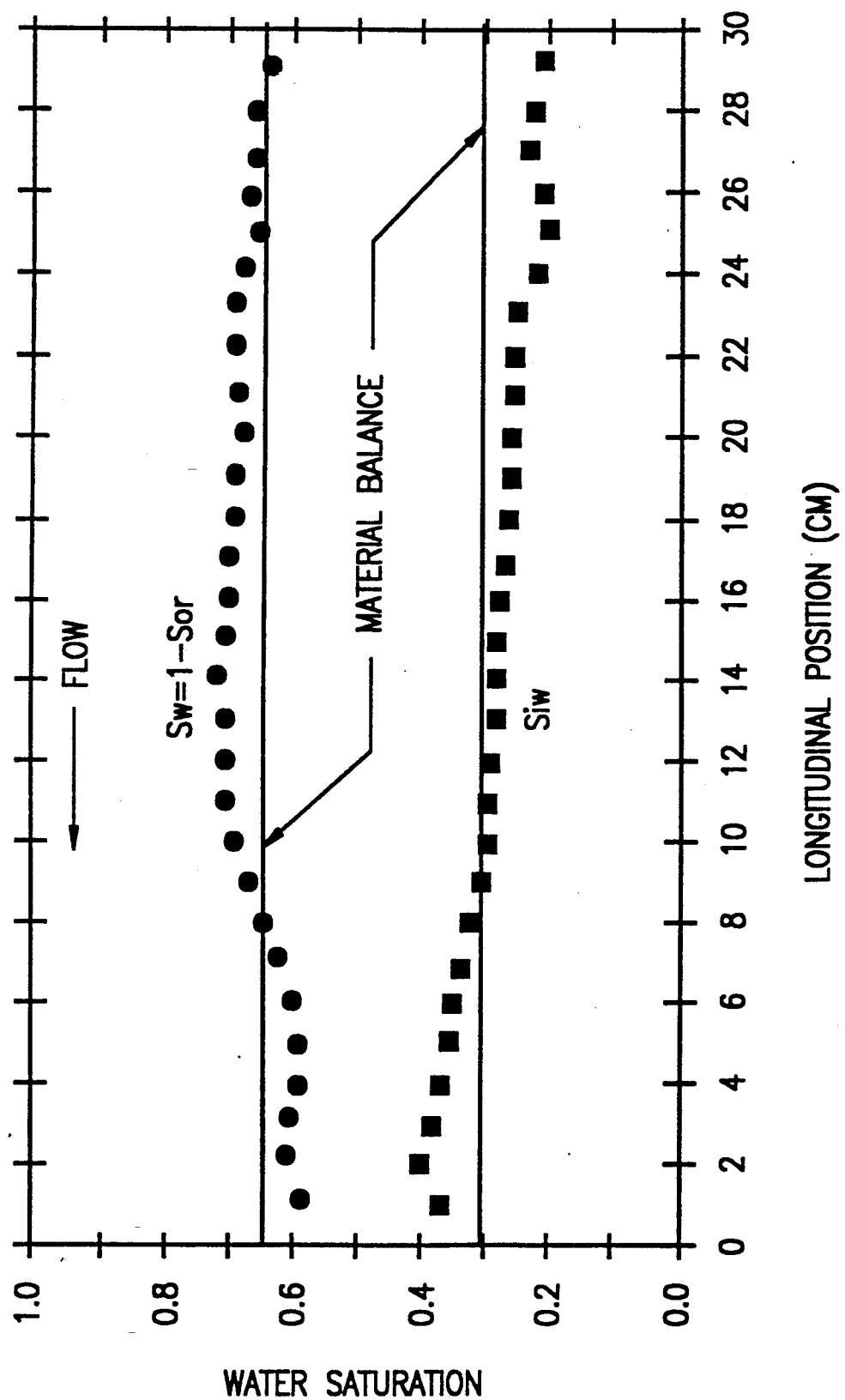
FIG. 6 is a graph presenting the relationship between water saturation and longitudinal position along a core sample for an experiment conducted in accordance with the method and system of the present invention.
Figure 7:
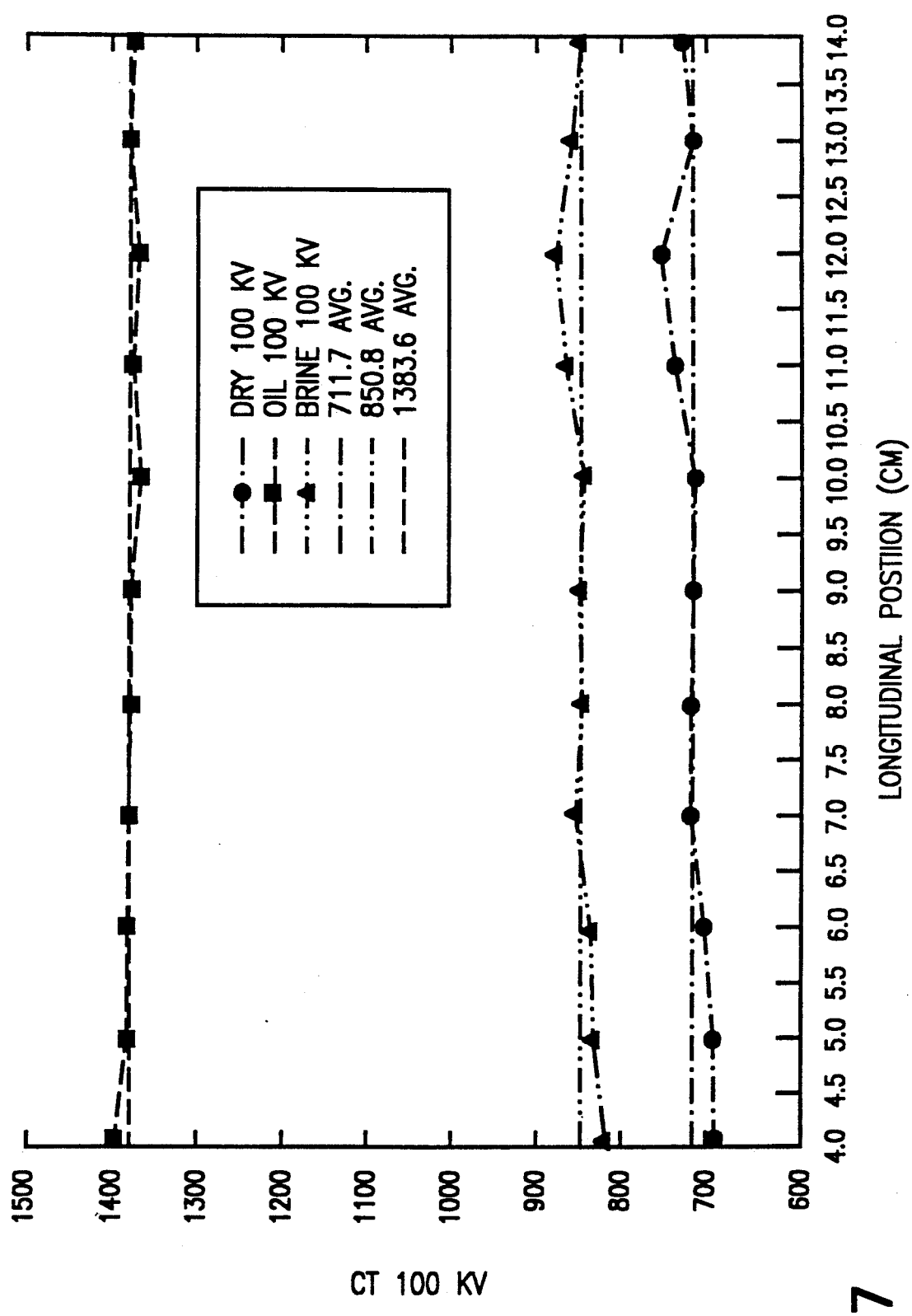
FIG. 7 is a graph presenting the relationship between CT number at 100 KV and longitudinal position along a core sample for a series of experiments conducted in accordance with the method and system of the present invention.
Figure 8:
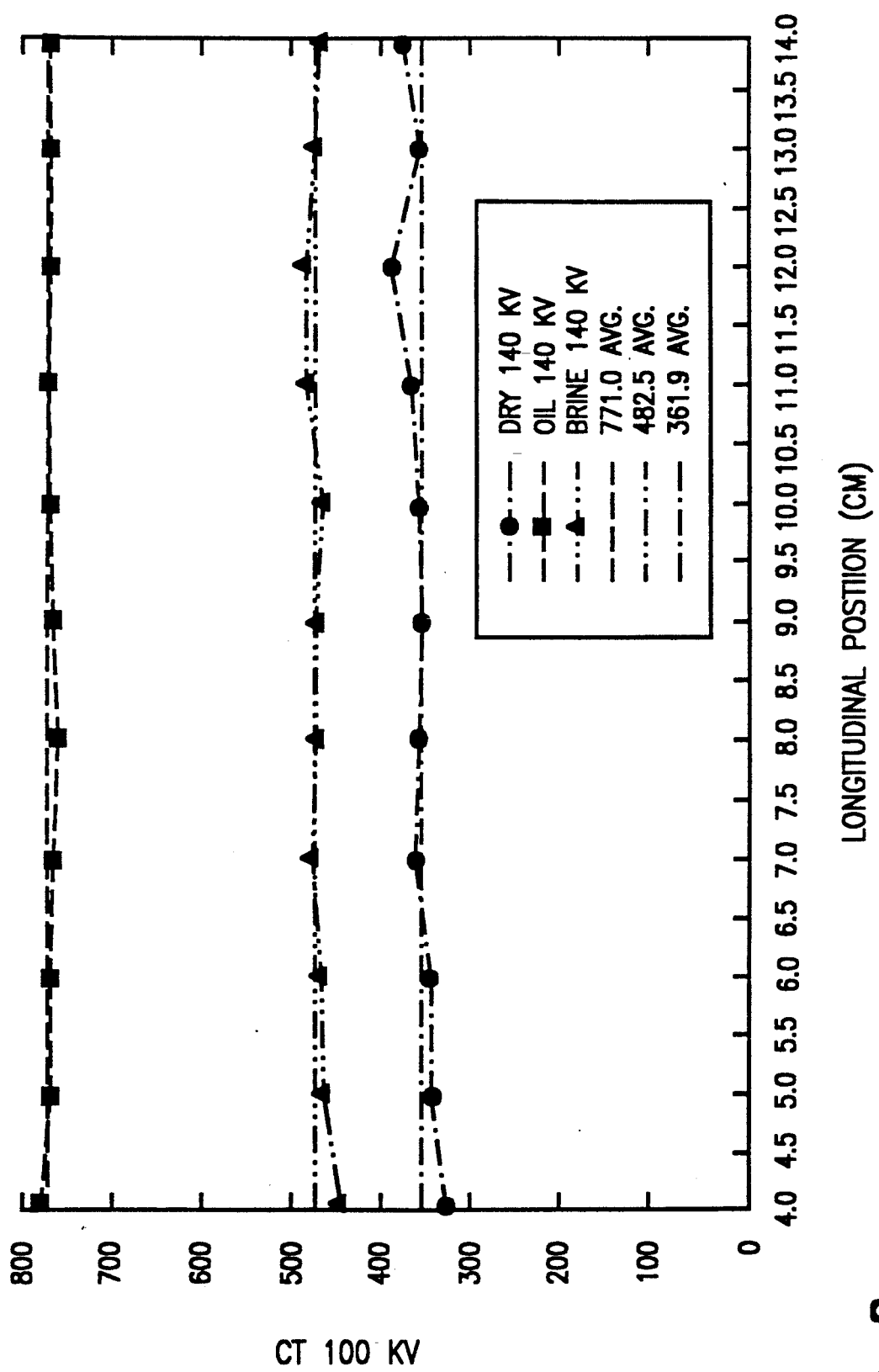
FIG. 8 is a graph presenting the relationship between CT number at 140 KV and longitudinal position along a core sample for a series of experiments conducted in accordance with the method and system of the present invention.

The Berea sample was saturated with barium bromide ($BaBr_2$) and flooded with hexadecane to immobile brine saturation ($S_{iw}$). The sample was CAT scanned over its entire length in one centimeter slices. The sample was then flooded with brine to residual oil saturation ($S_{or}$). CAT scanning was repeated. The 100 percent base case calibrations were used to determine the $S_{iw}$ and $S_{or}$ saturation profiles. These profiles are presented in FIG. 6. Also included in FIG. 6 are the material balance derived saturations shown as reference lines. Repeatability of the CAT scan tests after the core was flooded again to $S_{iw}$ was found to be excellent.

The volumetric material balance of the system was checked against the weight balance and results showed the agreement to be within 1.0 percent. Systematic calibration of the liquid pumps, gas flow meter, and pressure transducers shows the equipment was operating within the specified precision range. For the two-phase flow system, saturations computed from X-ray tomography agreed within one to two percent of the values calculated from material balance.

Example 2

This example demonstrates the utility of the system and method of the present invention in three-phase fluid testing.

Once again, the fluids used were selected to represent interfacial tension, gravity, density, and viscosity typical of a hydrocarbon reservoir. Hexadecane, barium bromide, and nitrogen were selected as the oil, brine, and gas phase, respectively.

Upon completion of the two-phase tests of Example 1, the Berea core, installed in flow cell assembly 100, was simultaneously injected with oil, gas, and brine at predetermined ratios until steady-state conditions were attained. The sample was CAT scanned at two different energy levels (100 KV and 140 KV). The CAT scan results at both energy levels showed the saturation to be uniformly distributed in all cases. Due to the lack of sufficient numerical differences in the energy-attenuation relationships between the three-phases, quantitative saturations were not well defined.

The volumetric material balance of the system was again checked against the weight balance and results showed the agreement to be within 1.0 percent. Systematic calibration of the liquid pumps, gas flow meter, and pressure transducers again demonstrated that the equipment was operating within the specified precision range. For the Example 2 tests, saturations computed from X-ray tomography agreed to within three to four percent of the material balance values. The repeatability of the CAT scan data was again very good.

The physical properties of the Berea sample and the fluid system employed in Examples 1 and 2 are presented in Table 1, below.

TABLE 1

PHYSICAL PROPERTIES OF BEREA SAMPLE AND FLUID PROPERTIES USED IN TESTS

| | | |
|---|---|---|
| SAMPLE: | Bulk Volume = | 617.71 cc |
| | Pore Volume = | 140.87 cc |
| | Porosity = | 22.8 percent |
| FLUIDS: | Fluids used in three-phase tests were | |
| | 20,000 ppm Barium Bromide, Hexadecane, and Nitrogen. | |
| DENSITY: | Barium Bromide = | 1.18 gm/cc |
| | Hexadecane = | 0.77 gm/cc |
| | Nitrogen = | 0.0012 gm/cc |
| VISCOSITY: | Barium Bromide = | 1.33 cp |
| | Hexadecane = | 3.02 cp |
| | Nitrogen = | 0.018 cp |

Example 3

This example demonstrates the utility of the system and method of the present invention in three-phase relative permeability testing using a Hanifa core sample.

The sample preparation, mounting and test procedures followed were as previously described for Examples 1 and 2. He fluids used in the tests were different than those used in the calibration tests to prevent formation of precipitates and formation plugging due to anhydrite conversion to gypsum.

Three-phase flow measurements were completed on a full-core sample from the Hanifa reservoir. The physical properties of the test sample and the properties of the fluids used in the tests are presented in Table 2, below.

TABLE 2

PHYSICAL PROPERTIES OF HANIFA SAMPLE AND FLUID PROPERTIES USED IN TESTS

| | | |
|---|---|---|
| SAMPLE: | Bulk Volume = | 399.61 cc |
| | Pore Volume = | 93.44 cc |
| | Porosity = | 23.40 percent |
| FLUIDS: | Fluids used in three-phase tests were | |
| | Brine - 50,000 ppm $CaCl_2$ (saturated with Calcium Sulfate) | |
| | Oil - 50/50 concentration Iodadecane/Hexadecane | |
| | Gas - Nitrogen | |
| DENSITY: | $CaCl_2$ = 1.03 gm/cc | |
| | Iodadecane/Hexadecane = 0.944 gm/cc | |
| | Nitrogen = 0.0012 gm/cc | |
| VISCOSITY: | $CaCl_2$ = 1.13 cp | |
| | Iodadecane/Hexadecane = 3.36 cp | |

TABLE 2-continued
PHYSICAL PROPERTIES OF HANIFA SAMPLE AND FLUID PROPERTIES USED IN TESTS Nitrogen = 0.018 cp Base CAT scan calibrations were made on the sample at 100 percent gas, brine, and oil saturations at energy levels of 100 and 140 KV. These calibrations are shown in FIGS. 5 and 6. The uniformity of the CT numbers along the length of the core sample confirm homogeneity of the core sample.

The calculated relative permeability and fluid saturation data are presented in Table 3, below. A review of the three-phase flow data presented in Table 3 suggest water-wet behavior. The minimum interstitial water saturation ($S_{iw}$) after the oil flood was 32.6 percent. The minimum interstitial water saturation after co-injection of gas-oil decreased to a value of 23.3 percent at a gas saturation of 22.6 percent. The residual oil saturation ($S_{or}$) after the waterflood was 11.3 percent as compared to 19.4 percent after the gas flood. The lower $S_{or}$ value after waterflood is expected due to the more favorable mobility ratio between water and oil as compared to gas and oil.

TABLE 3
THREE-PHASE RELATIVE PERMEABILITY DATA HANIFA RESERVOIR SAMPLE

| $K_g$ (mds) | $S_g$ (%) | $K_{rg}$ | $K_o$ (mds) | $S_o$ (%) | $K_{ro}$ | $K_w$ (mds) | $S_w$ (%) | $K_{rw}$ |
|---|---|---|---|---|---|---|---|---|
| 954 | 100 | 1.0 | 0.0 | 0 | 0.0 | 0.0 | 0 | 0.0 |
| 0 | 0 | 0 | 0 | 0 | 0.0 | 900 | 100 | 1.0 |
| 0 | 0 | 0 | 830 | 67.4 | 0.922 | 0 | 32.6 | 0.0 |
| 300.0 | 34.8 | 0.333 | 0 | 19.4 | 0 | 0 | 45.8 | 0 |
| 147.6 | 17.0 | 0.1640 | 250.7 | 54.7 | 0.2786 | 0 | 28.3 | 0 |
| 45.9 | 16.1 | 0.0510 | 232.3 | 57.5 | 0.2581 | 0 | 26.4 | 0 |
| 15.6 | 22.6 | 0.0170 | 243.3 | 54.1 | 0.2704 | 0 | 23.3 | 0 |
| 0.6 | 7.2 | 0.0007 | 48.6 | 43.0 | 0.0540 | 4.1 | 49.8 | 0.0046 |
| 0.3 | 1.7 | 0.0003 | 37.4 | 42.2 | 0.0416 | 6.3 | 56.1 | 0.0070 |
| 0.3 | 4.4 | 0.0003 | 17.2 | 30.7 | 0.0191 | 5.8 | 64.9 | 0.0064 |
| 0.9 | 9.3 | 0.0010 | 12.7 | 28.2 | 0.0141 | 4.3 | 62.5 | 0.0048 |
| 4.6 | 14.7 | 0.0050 | 6.4 | 22.8 | 0.0071 | 2.2 | 62.5 | 0.0024 |
| 98.5 | 26.8 | 0.1094 | 15.9 | 27.8 | 0.0177 | 0.2 | 45.4 | 0.0002 |
| 0 | 0 | 0 | 0 | 11.3 | 0.0 | 356 | 88.7 | 0.396 |

Although the present invention has been described With preferred embodiments, it is to be understood that modifications and variations may be utilized without departing from the spirit and scope of this invention, as those skilled in the art will readily understand. Such modifications and variations are considered to be within the purview and scope of the appended claims.

What is claimed is:

1. A system for use in determining multi-phase fluid saturation in a porous media comprising:
    (a) means for containing the porous media, said porous media containing means having a fluid inlet positioned at a first end thereof and a fluid outlet positioned at a second end thereof;
    (b) a fluid separatory vessel for separating the multi-phase fluid into at least a first fluid phase and a second fluid phase, said vessel having an inlet in fluid communication with said fluid outlet of said media containing means and at least a first outlet and a second outlet, wherein said first outlet and said second outlet of said vessel are positioned to permit withdrawal of the separated first fluid phase and the separated second fluid phase, respectively;
    (c) means for measuring pressure across said porous media;
    (d) a first pumping means in fluid communication with said first outlet of said fluid separatory vessel for withdrawing the separated first fluid phase therefrom for transfer to said fluid inlet of said media containing means;
    (e) a second pumping means in fluid communication with said second outlet of said fluid separatory vessel for withdrawing the separated second fluid phase therefrom for transfer to said fluid inlet of said media containing means;
    (f) means for measuring fluid flow of the separated first fluid phase in transfer from said first outlet of said fluid separatory vessel to said fluid inlet of said media containing means; and
    (g) means for measuring fluid flow of the separated second fluid phase in transfer from said second outlet of said fluid separatory vessel to said fluid inlet of said media containing means.

2. The system of claim 1, further comprising means for supplying a gaseous fluid to said fluid inlet of said media containing means 3. The system of claim 2, wherein said fluid separatory vessel has a third fluid outlet positioned to permit withdrawal of the separated gaseous fluid phase.

4. The system of claim 3, further comprising means for measuring the flow rate of the gaseous fluid supplied to said fluid inlet of said media containing means.

5. The system of claim 4, wherein said means for sensing pressure across said porous media comprises a pressure transducer.

6. The system of claim 5, wherein said means for measuring pressure within said porous media containing means comprises a first set of piezoelectric pressure transducers and a second set of piezoelectric pressure transducers positioned to enable pressure drop across the porous media to be measured.

7. The system of claim 1, wherein said means for measuring pressure within said porous media containing means comprises a first set of piezoelectric pressure transducers and a second set of piezoelectric pressure transducers positioned to enable pressure drop across the porous media to be measured.

8. The system of claim 1, wherein said porous media containing means is constructed substantially from an X-ray transparent material.

9. The system of claim 8, wherein said porous media containing means is constructed substantially from a methacrylate ester polymeric material.

10. The system of claim 1, further comprising a computer-controlled data acquisition system.

11. A method for determining multi-phase relative permeability of a porous media, comprising the steps of:
   (a) establishing a multi-phase fluid flow condition through the porous media, the multi-phase fluid having at least a first phase having a first density and a second phase having a second density;
   (b) measuring the pressure drop across the length of the porous media;
   (c) collecting the multi-phase fluid in a fluid separatory vessel;
   (d) separating the multi-phase fluid within the fluid separatory vessel;
   (e) recirculating at least one phase of the multi-phase fluid separated in step (d) to the porous media;
   (f) repeating steps (a) through (e) until steady-state flow conditions by phase are obtained;
   (g) determining fluid saturation within the porous media; and
   (h) determining the relative permeability of the porous media from said measurements of pressure and fluid saturation.

12. The method of claim 11, wherein the multi-phase fluid further has a third phase.

13. The method of claim 12, wherein the first phase of the multi-phase fluid is a liquid hydrocarbon and the second phase of the multi-phase fluid comprises water or brine.

14. The method of claim 13, wherein the third phase is a gas.

15. The method of claim 14, wherein the gas is inert.

16. The method of claim 15, wherein the inert gas is nitrogen.

17. The method of claim 16, further comprising the step of saturating the porous media with a saturation agent prior to conducting step (a).

18. The method of claim 11, further comprising the step of saturating the porous media with a saturation agent prior to conducting step (a).

19. The method of claim 18, wherein step (a) is conducted until there is irreducible saturation of the porous media by said saturating agent.

20. The method of claim 11, wherein the first phase of the multi-phase fluid is a liquid hydrocarbon and the second phase of the multi-phase fluid comprises water or brine.

* * * * *